United States Patent [19]

Hirayama et al.

[11] 4,377,460
[45] Mar. 22, 1983

[54] SOLID ELECTROLYTE GAS SENSING APPARATUS

[75] Inventors: Chikara Hirayama, Murrysville Boro; Ching-Yu Lin, Monroeville, both of Pa.

[73] Assignee: Westinghouse Electric Corp., Pittsburgh, Pa.

[21] Appl. No.: 312,552

[22] Filed: Oct. 19, 1981

[51] Int. Cl.³ ............................................. G01N 27/46
[52] U.S. Cl. ................................. 204/195 S; 204/1 T
[58] Field of Search ............................. 204/1 S, 195 S

[56] References Cited

U.S. PATENT DOCUMENTS

| | | | |
|---|---|---|---|
| 3,546,086 | 12/1970 | Sayles | 204/195 S |
| 3,776,831 | 12/1973 | Roy et al. | 204/195 S |
| 3,791,937 | 2/1974 | Besson et al. | 204/1 S |
| 4,088,543 | 5/1978 | Ruka | 204/195 S |
| 4,186,072 | 1/1980 | Blumenthal | 204/195 S |
| 4,300,991 | 11/1981 | Chiba et al. | 204/195 S |
| 4,302,312 | 11/1981 | Ishitani et al. | 204/195 S |
| 4,305,803 | 12/1981 | Beyer et al. | 204/195 S |

FOREIGN PATENT DOCUMENTS 2556483  3/1977  Fed. Rep. of Germany ... 204/195 S

Primary Examiner—T. Tung
Attorney, Agent, or Firm—M. P. Lynch

[57] ABSTRACT

An alkali ion conductive solid electrolyte electrochemical concentration cell assembly for measuring gases containing anhydrides or related compounds in air or in oxygen-bearing gases is divided into two identical alkali ion conductive half cycles. Each half cell is secured to opposite surfaces of the closed end of a solid membrane exhibiting alkali ion conductivity corresponding to the alkali ion conductivity of the half cells. The membrane effectively isolates a monitored gas environment contacting one half cell from a reference gas environment contacting the other half cell while supporting the equilibrium mode of operation of the concentration cell assembly to generate an electrical signal indicative of a gas species of interest in the monitored gas environment.

5 Claims, 4 Drawing Figures

SOLID ELECTROLYTE GAS SENSING APPARATUS

BACKGROUND OF THE INVENTION

The requirements for monitoring and controlling stack gas pollutants have resulted in the development of solid electrolyte gas sensors having electrolyte compositions uniquely responsive to gaseous pollutants such as $SO_2$, $CO_2$ and $NO_2$. Solid electrolyte sensors for monitoring gases containing anhydrides or related compounds in air or in oxygen-bearing gases have been described in detail in Canadian Pat. Nos. 1,002,599 and 1,040,264, both of which have been assigned to the assignee of the present invention and are incorporated herein by reference. The above-referenced sensors are electrochemical concentration cells which sense the equilibrium of a gas species of interest and generate an EMF signal corresponding to the difference in partial pressure of the gas species across the solid electrolyte sensor. Typically, the solid state sensor includes an ion conductive solid electrolyte with electrodes disposed on opposite surfaces thereof. The stack gas, or monitored gas environment, contacts a sensing electrode while the opposite electrode serves as a reference electrode. Conventional solid electrolyte compositions require operating temperatures of between about 600° C. and 900° C. to exhibit the desired ion conductivity to generate a suitable EMF signal. The accuracy of the EMF measurement depends in part on the effective sealing, or isolation, of the reference electrode from the monitored gas environment contacting the sensing electrode of the electrochemical cell. This isolation, or sealing requirement, at elevated operating temperatures has resulted in numerous expensive and complicated designs to achieve the desired isolation.

SUMMARY OF THE INVENTION

There is described herein with reference to the accompanying drawings a simple and effective technique for providing the desired isolation between the monitored gas environment and the reference environment of a solid electrolyte electrochemical cell assembly. The solid electrolyte cell assembly consists of two identical half cells, each consisting of a disc electrolyte element having an electrode disposed in intimate contact with one surface thereof. The opposite surfaces of the solid electrolyte disc elements are secured in contact with the opposite surfaces of the closed end of a closed-end solid tubular membrane of a material composition exhibiting ion conductivity at elevated temperatures which corresponds to the ion conductivity of the solid electrolyte elements. A combination of the closed-end tubular membrane and the identical solid electrolyte half cells are positioned within a housing which provides a reference gas environment for contacting one of the solid electrolyte half cells and a monitored gas environment to contact the other solid electrolyte half cell. The closed-end tubular ceramic membrane effectively isolates the reference gas environment from the monitored gas environment while supporting the desired ion conductivity of the solid electrolyte electrochemical cell.

BRIEF DESCRIPTION OF THE DRAWINGS

The invention will become more readily apparent from the following exemplary description in connection with the accompanying drawings.

DESCRIPTION OF THE PREFERRED EMBODIMENT

Figure 1A:
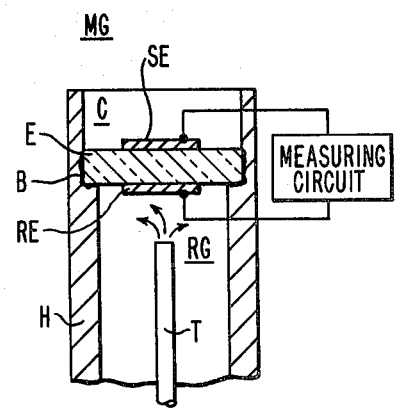
FIGS. 1A and 1B are sectioned schematic illustrations of prior art gas probe assemblies containing a solid electrolyte electrochemical cell gas sensor.
Figure 1B:
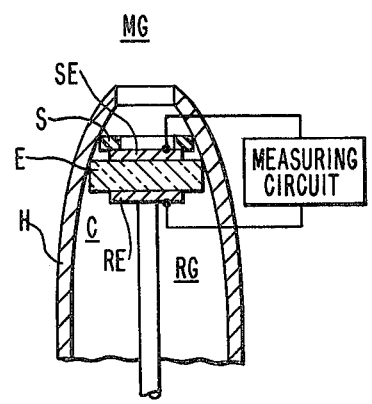

Referring to FIGS. 1A and 1B there are illustrated typical Prior Art techniques for securing a solid electrolyte electrochemical cell C within a tubular housing H so as to isolate the monitored gas environment MG which contacts the sensing electrode SE of the cell C from the reference gas environment RG which contacts the reference electrode RE of the cell C. The solid electrolyte electrochemical cell includes a solid electrolyte member E which exhibits ion conductivity at elevated temperatures suitable to generate an electrical signal indicative of a selected gas species of the monitored gas environment. The EMF signal developed by the concentration cell C is measured by the measuring circuit MC connected across the electrodes SE and RE. Suitable alkali cation conductive solid electrolyte compositions can be selected to render the solid electrolyte electrochemical cell C suitable for measuring $SO_2$, $CO_2$, $NO_2$, etc. Commercially available oxygen-measuring cells typically employ oxygen anion conductive stabilized zirconia as the electrolyte material. A detailed description of oxygen anion conductive material compositions and concentration cell configurations suitable for oxygen measurements using solid electrolyte electrochemical cells is provided in U.S. Pat. No. Re. 28,792 which is assigned to the assignee of the present invention and is incorporated herein by reference. Suitable electrolyte compositions for supporting alkali cation conductivity for the measurement of $SO_2$ in the monitored gas environment include $K_2SO_4$ and $Na_2SO_4$. Electrolyte compositions comprising $Na_2CO_3$ and $NaNO_3$ provide electrochemical cell ion conductivity to produce an EMF signal indicative of the $CO_2$ and $NO_2$ content respectively of a monitored gas environment.

The EMF signal developed by the solid electrolyte electrochemical concentration cell C is developed in accordance with the well-known Nernst equation wherein the variables include the cell temperature, and the variation of partial pressure of the gas constituent of interest at both the sensing electrode SE and the reference electrode RE. In order to eliminate the cell temperature and the change in the partial pressure of gas constituent of the reference gas RG as variables, the cell temperature is maintained essentially constant and the partial pressure of the gas constituent of the reference gas RG is maintained at a known or constant level. The temperature of the cell C can be maintained constant by a temperature controlled furnace, or, in the alternative, variations in temperature can be compensated for electronically in circuitry associated with the measuring circuit MC. In order to maintain the partial pressure of the gas constituent of interest constant or known in the reference gas environment RG it is essential to effectively seal the cell C within the housing H so as to avoid leakage of the monitored gas environment MG into the reference gas environment RG. This is accomplished in FIG. 1A through the use of a bonding material B for securing the electrochemical cell C within the tubular housing H. Due to the fact that the typical cell operating temperature is between about 600° C.–900° C. such bonding materials may deteriorate due to the elevated temperatures and the reaction of the bonding material B with the elements in an often-times corrosive industrial gas environment. Similar sealing problems are encountered when a metal, i.e. gold, or an elastomeric sealing ring S, such as illustrated in FIG. 1B, is employed to provide a gas-tight seal between the monitored gas environment MG and the reference gas environment RG.

In the embodiment of FIG. 1B an adjustable rod member R secures the cell C in compression contact with the elastomer ring seal S to achieve the desired isolation between the monitored gas environment MG and the reference gas environment RG. Once again the high temperature operation and the corrosive elements of the typical industrial environments that constitute the monitor gas environment MG have a deleterious effect on the seal S over a period of time.

Figure 2:
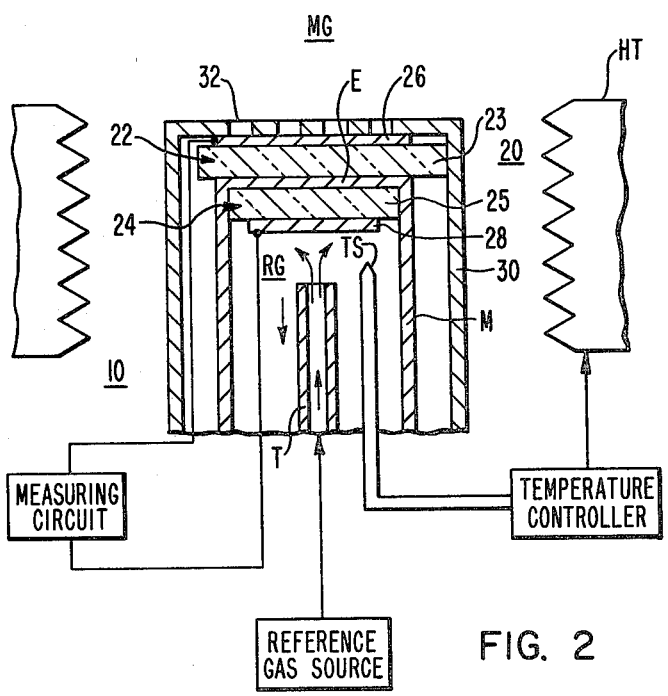
FIG. 2 is an enlarged sectioned illustration of a gas probe assembly incorporating a solid electrolyte electrochemical cell assembly in accordance with the disclosed inventive technique; and, FIG. 3 is a sectioned illustration of a novel assembly of FIG. 2 within a gas probe housing.

It has been determined experimentally that the above sealing problem can be essentially eliminated in alkali ion conductive concentration cells through the use of an alkali ion conductive membrane M as shown in the gas probe assembly 10 of FIG. 2. The solid electrolyte electrochemical concentration cell assembly 20 consists of identical alkali ion half cells 22 and 24 comprised of solid electrolyte element 23 and sensing electrode 26, and solid electrolyte element 25 and reference electrode 28 repectively. The half cells 22 and 24 are secured to opposite surfaces of the closed end E of the closed-end tubular membrane M. The sensing electrode 26 of the electrochemical cell assembly 20 is disposed in contact with a surface of the electrolyte element 23 opposite from the surface contacting the membrane M, while the reference electrode 28 is in intimate contact with the surface of the electrolyte element 25 opposite the electrolyte element surface contacting the membrane M. The electrochemical cell assembly 20, consisting of identical alkali ion conductive half cells 22 and 24, is located within the tubular housing 30 having apertures 32 therein to permit the monitored gas environment MG to enter the housing 30 and contact the sensing electrode 26. A reference gas RG, having a stable or known concentration of the gas constituent to be measured, is supplied by an inlet tube T from a remote reference gas source RS for contact with the reference electrode 28. The EMF signal developed by the concentration cell 20 in response to a difference, or change in equilibrium, in the partial pressure of the gas constituent of interest, as measured between the sensing electrode 26 and the reference electrode 28, is manifested by the measuring circuit MC. A temperature controller TC responds to the electrochemical cell operating temperature as measured by the temperature sensor TS to control the heater H to maintain the operating temperature of the cell 20 essentially constant.

The closed-end tubular membrane M is a solid composition, i.e. ceramic, glass, etc., exhibiting alkali ion conductivity at elevated temperatures which corresponds to the alkali ion conductivity of the electrolyte elements 23 and 25. Experimental evaluation has confirmed that most ceramics incorporate some alkali oxide, such as $K_2O$ and $Na_2O$, in an amount up to a few percent. These ceramic materials become $K^+$ and $Na^+$ ionic conductors at elevated temperatures corresponding to the operating temperature of the solid electrolyte electrochemical cell assembly 20. Thus, the combination of an alkali ion conductive closed-end tubular membrane M with alkali ion conductive electrolyte elements 23 and 25 of identical half cells 22 and 24 for monitoring $SO_2$, $CO_2$, etc. provides the required isolation between the monitored gas environment MG and the reference gas environment RG while supporting the necessary alkali ion conduction between the electrode SE and RE. In the event the identical electrolyte elements 23 and 25 are $K_2SO_4$, a solid composition for membrane M would be selected which exhibits $K^+$ ion conductivity. Similarly, if the electrolyte elements 23 and 25 are comprised of $Na_2So_4$ then the alkali oxide material selected for the membrane M would be one which exhibits $Na^+$ ion conductivity. Ceramic compositions of beta-alumina ($\beta$-$AL_2O_3$) and beta, double prime-alumina ($\beta''$-$Al_2O_3$) are sodium ion conductors and are thus best suited for use as membranes M in combination with sodium salt electrolyte elements 23 and 25, such as $Na_2SO_4$ and $Na_2CO_3$, to form electrochemical concentration cells for the measurement of $SO_2$ and $CO_2$ respectively. While there are numerous solid materials exhibiting alkali oxide content which render them suitable for use as a membrane M, a preferred membrane material is mullite. Mullite is a relatively inexpensive material which not only exhibits $K^+$ ion conductivity, but is mechanically strong and capable of extended use at elevated temperatures. Furthermore mullite is inert to corrosive liquids and gases such as nitric and sulfuric acid which are often present in industrial stack gas environments constituting the monitored gas environment MG.

Figure 3:
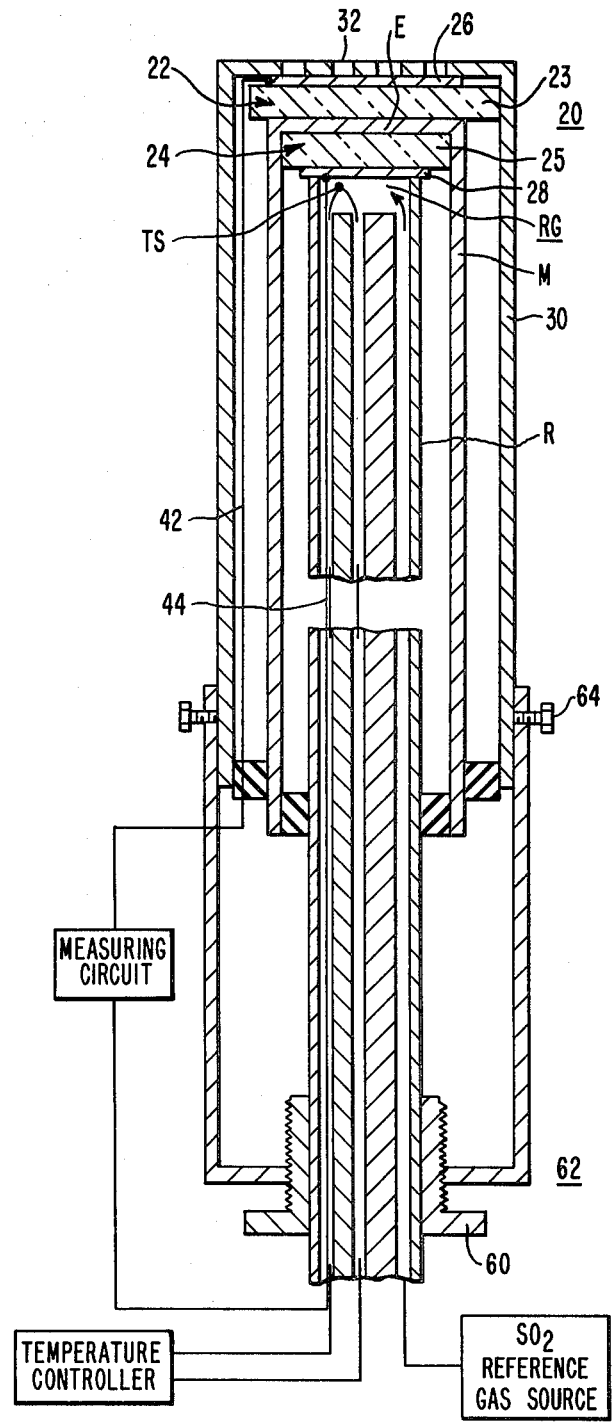

A preferred mechanical assembly of the gas probe apparatus 10 is illustrated in FIG. 3. The solid electrolyte element 23 of half cell 22 is first cemented onto the external surface of the closed end E of the alkali ion conductive tubular membrane M. A platinum screen is formed around the surface of the solid electrolyte element 23 to form a porous, resilient sensing electrode 26. The tubular ceramic membrane M is then inserted within the protective housing 30 with the electrode 26 contacting the apertured end 32 of the housing of the tubular housing 30. A small quantity of solid electrolyte powder, i.e., $K_2SO_4$, is positioned on the internal surface of the closed end E of the alkali ion conductive solid membrane M to assure the desired contact with the solid electrolyte element 25 of half cell 24 which is mechanically inserted into the membrane M and in contact with the closed end thereof. Platinum screen material secured to the end of a tubular rod member R serves as a porous, resilient reference electrode 28. The tubular rod member R, which may be typically constructed of alumina, includes passages to accommodate the temperature sensor TS, electrode leads 42 and 44, and the flow of the reference gas from a remote reference gas source through the porous platinum screen electrode comprising reference electrode 28 to produce the reference gas environment RG. In the event the solid electrolyte elements 23 and 25 consist of $K_2SO_4$ compositions, the reference gas environment RG would be an $SO_2$ gas environment and the ceramic material comprising the membrane M would exhibit $K^+$ ion conductivity. The combination of the tubular rod member R and the electrode 28 secured to the open end thereof is separately inserted within the tubular membrane M. The opposite end of the rod member R is attached to a threaded manual screw adjustment 60 of a mechanical mounting fixture 62 which is secured to the outside surface of the tubular housing 30 by set screws 64. The fixture 60 aligns the rod member R within the tubular ceramic membrane M and the rotation of the screw adjustment 60 applies mechanical pressure against the combination of the half cell 24, the closed end E of the tubular membrane M, and the half cell 22 to mechanically secure the combination in contact with the apertured end 32 of the tubular housing 30. This arrangement permits easy removal and replacement of the membrane M and the half cells 22 and 24. Electrical leads 42 and 44 extend from electrodes 26 and 28 respectively to the EMF measuring circuit MC.

We claim:

1. A gas analyzer apparatus for measuring gases of a monitored gas environment which contain anhydrides or related compounds in air or in oxygen-bearing gases by generating an electrical signal on the basis of a difference in the partial pressure of a gas species between the monitored gas environment and a reference gas environment, comprising, a solid electrolyte electrochemical concentration cell assembly including first and second identical half cells, each half cell consisting of an alkali ion conductive electrolyte element and an electrode disposed on a surface thereof, and a solid membrane means of a composition exhibiting alkali ion conductivity corresponding to the alkali ion conductivity of said half cells, the surface of said first half cell opposite the electrode being in contact with a first surface of said membrane means, the surface of said second half cell opposite the electrode being in contact with an opposite surface of said membrane means, said monitored gas environment contacting said first half cell and said reference gas environment contacting the second half cell, said solid membrane means isolating said monitored gas environment from said reference environment while supporting the alkali ion conductivity of the concentration cell assembly.

2. Apparatus as claimed in claim 1 wherein said solid membrane means is a closed end tubular member with said first half cell disposed in contact with one side of the closed end and said second half cell disposed in contact with the other side of the closed end.

3. Apparatus as claimed in claim 1 wherein said solid membrane means is a ceramic composition.

4. Apparatus as claimed in claim 1 wherein said solid membrane means is a mullite composition.

5. A gas analyzer apparatus for measuring gases of a monitored gas environment which contain anhydrides or related compounds in air or in oxygen-bearing gases by generating an electrical signal on the basis of a difference in the partial pressure of a gas species between the monitored gas environment and a reference gas environment, comprising, a solid electrolyte electrochemical concentration cell assembly including first and second identical half cells, each half cell including an alkali ion conductive electrolyte element, a closed end tubular support means, the closed end having apertures therethrough, said first half cell further including a sensing electrode in contact with a surface of the electrolyte element, said first half cell being positioned within said tubular support means with said sensing electrode disposed between the apertured closed end and the electrolyte element, a closed end tubular membrane means of a composition exhibiting alkali ion conductivity corresponding to the alkali ion conductivity of said electrolytes of said first and second half cells, said membrane means being positioned within said support means with the closed end of said membrane means contacting a surface of the electrolyte element of said first half cell which is opposite said sensing electrode, said second half cell including a reference electrode in contact with a surface of the electrolyte element of said second half cell, said second half cell being positioned within said closed end tubular solid membrane means with a surface of the electrolyte element opposite said reference electrode contacting the surface of the closed end of said membrane means opposite the surface of the closed end of said membrane means being contracted by said first half cell, reference means for establishing a reference gas environment in contact with said reference electrode, said closed end tubular solid membrane means isolating said monitored gas environment contacting said sensing electrode from the reference gas environment contacting said reference electrode, and circuit means connected between said sensing electrode and said reference electrode to generate an electrical signal measurement of a gas species of said monitored gas environment.

* * * * *